June 16, 1936. E. C. TRAUERNICHT Plant Pat. 184
POMEGRANATE
Filed Jan. 29, 1936
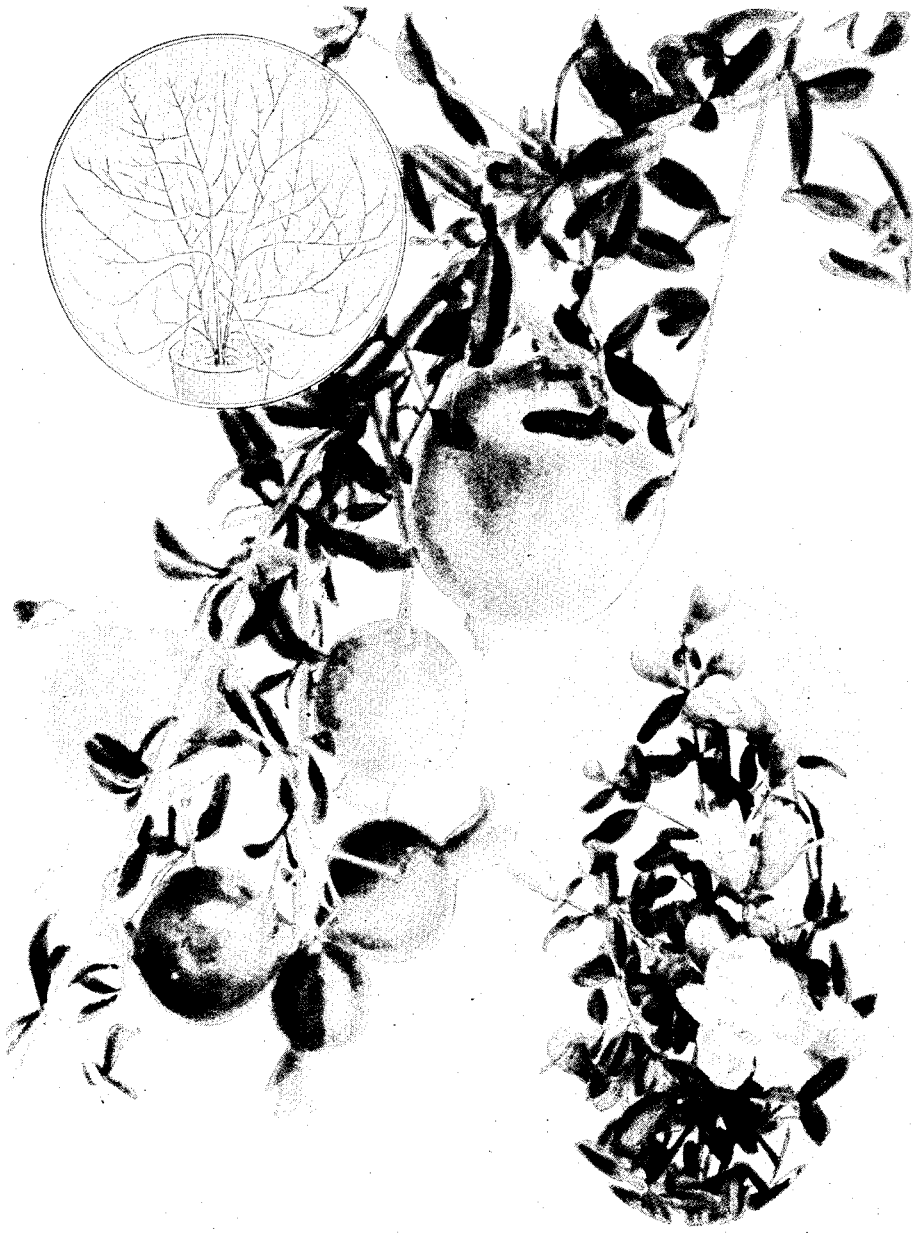
Inventor
E. C. Trauernicht
By Robb & Robb
Attorneys Patented June 16, 1936 Plant Pat. 184

UNITED STATES PATENT OFFICE

184

POMEGRANATE

Erich C. Trauernicht, Fort Worth, Tex., assignor to Baker Bros. Company, Fort Worth, Tex., a corporation Application January 29, 1936, Serial No. 61,390

1 Claim. (Cl. 47—62)

The commonly known dwarf pomegranate, a form of the acid variety of *Punica granatum* of which my semi-dwarf pomegranate is a chance seedling, ordinarily grows to a height of about eighteen inches in the region of Texas, though the limit of its growth varies within narrow limits throughout other sections of the southern portion of the United States and south of the 36th parallel of latitude in other parts of the world. By way of contrast, my new variety attains an ultimate height of approximately four feet in Texas. It will, therefore, be apparent that my new variety grows to a size about four times that of the common dwarf pomegranate, grown under comparable conditions.

While the comon dwarf pomegranate, as distinguished from my semi-dwarf pomegrante, has fruit about the size of a large marble, the fruit of my new variety is about four times as large. Besides its characteristic larger size the fruit of my new variety has a further distinctive characteristic in that during the process of its development to maturity it changes in color from green to dark red, displaying at various times all the intermediate shades. During the ripening period fruit in various stages of development will be found on a single shrub displaying shades of color, ranging from green to dark red, corresponding to their respective stages, the whole producing a vari-colored effect which greatly enhances the beauty of the shrub throughout this period.

A further distinguishing characteristic of my new variety is its habit of unusually hardy growth. Whereas the common dwarf pomegranate, while maintaining the habit of hardiness of the species *Punica granatum* in semi-tropical climates, is, nevertheless, subject to the killing effect of freezing temperatures, being readily frozen to the ground and often killed outright in very cold weather, my new variety is not affected by ordinary freezes.

Aside from the distinguishing features pointed out herein, the habits of growth, general appearance and other characteristics of my new variety are generally similar to the dwarf pomegranate already known.

My new variety of dwarf pomegranate was discovered as a chance seedling in a seed bed of dwarf pomegrante, a form of the acid variety of *Punica granatum,* and, being asexually reproduced, it was discovered that the above described new and distinct characteristics were permanent attributes of the plant.

It is thought that my semi-dwarf pomegranate may be a cross between the dwarf pomegranate, above referred to, and the old variety of fruiting pomegranate. However, my new variety is readily distinguishable from the latter. Whereas the fruiting pomegranate is upright in growth and has larger leaves more sparsely placed, my semi-dwarf has willowy, drooping stems, small leaves, and does not grow as tall as the fruiting pomegranate.

The following is a detailed description of my new variety of dwarf pomegranate:—

All references to color refer to Ridgway Chart, Plates I and II.

*Type.*—Hardy; semi-dwarf—seedling; for cut flowers and garden decoration.

*Flower*

*Locality where grown.*—Ft. Worth, Texas.

*Flowers borne.*—Several to stem, in cluster, on normal, semidrooping medium stems.

*Quantity of bloom.*—Abundant—outdoors.

*Continuity.*—Continuous, July 1 to Dec. 1.

Bud:—

*Peduncle.*—Medium; medium thickness; bending; reddish; smooth.

*Before calyx breaks.*—Size—small; form—ovoid; without appendages on the surface of the bud.

*As calyx breaks.*—Color: bud is Scarlet Red to Scarlet at base.

*As first petal opens.*—Size—small; form—ovoid.

*Color.*—Outside: Scarlet at tips, blending through Grenadine Red and Flame Scarlet to Orange Chrome in the throat of the flower. Inside: same as outside.

*Opening.*—It opens up well.

*Behavior.*—Persist.

*Flower longevity.*—On bush in garden 5 days in October, cut flower—grown outdoors, kept at living room temperatures 7 days in October.

Bloom:—

*Size.*—Medium, 1 to 1½ inches.

*Petalage.*—Single row of petals, arranged regularly.

*Form.*—Cupped, petals rolled outward.

*Petals.*—Soft; outside crepe-like; shape—oval.

*Color.*—Outside: Scarlet at tips, blending through Grenadine Red and Flame Scarlet to Orange Chrome in the throat of the flower. Inside: Same as outside.

This description of the flower was made from a pomegranate grown outdoors in October, 1935, at Fort Worth, Texas.

*Color.*—Outside: Scarlet at tips blending through Grenadine Red and Flame Scarlet to Orange Chrome in the throat of the flower.

(Ridgway Chart Plates I and II.) Inside: Scarlet of Plate I. Anthers—Flame Scarlet of Plate II. Filaments: Orange Chrome of Plate II.

*General color effect.*—Newly opened flower: Scarlet at tips, blending through Grenadine Red and Flame Scarlet to Orange Chrome in the throat of the flower. Three days open: Same as newly opened flower.

*Fruit*

*Form.*—Globular.
*Calyx.*—Crown-like.
*Seeds.*—Numerous, arranged in segments.
*Pulp.*—Bright crimson or pink-colored.
*Skin.*—Very thin, very acid.

*Reproductive organs*

*Stamens.*—Many; arranged irregularly.
*Filaments.*—Medium; yellow; many without anthers.
*Pollen.*—Moderate; yellow.
*Pistils.*—Many.
*Styles.*—Uneven, medium length; medium thickness; bunched.
*Stigma.*—Yellow.
*Ovaries.*—All enclosed in calyx.
*Hips.*—Pear-shaped; russet; smooth; fleshy.
*Sepals.*—Permanent; long.
*Seeds.*—Many; large.

*Plant*

Foliage:
*Leaves.*—Simple.
*Color.*—Mature: Upper surface dark green; under surface light green. Young: Upper surface dark green; under surface light green.
*Disease.*—Resistant to mildew and blackspot.

*Growth*

*Habit.*—Semi-dwarf—bushy; much branched.
*Growth.*—Vigorous.
*Canes.*—Heavy.
Main stems.—Green.
*Thorns.*—Few; long.
*Prickles.*—None.
*Hairs.*—None.
Branches.—Green.
*Thorns.*—None.
*Prickles.*—None.
*Hairs.*—None.
New shoots.—Bright.

I claim:

A new and distinct variety of dwarf-acid pomegranate plant, substantially as shown and described, characterized by its unusually tall and vigorous growing habit, the largeness of its fruit and the vari-colored effect produced during the ripening period of said fruit.

ERICH C. TRAUERNICHT.